United States Patent [19]

Stühler et al.

[11] Patent Number: 4,801,730

[45] Date of Patent: Jan. 31, 1989

[54] PROCESS FOR THE PREPARATION OF FATTY ACID NITRILES AND GLYCEROL FROM GLYCERIDES

[75] Inventors: Herbert Stühler, Burgkirchen; Kurt Fischer, Neuötting, both of Fed. Rep. of Germany

[73] Assignee: Hoechst Aktiengesellschaft, Frankfurt am Main, Fed. Rep. of Germany

[21] Appl. No.: 122,403

[22] Filed: Nov. 19, 1987

[30] Foreign Application Priority Data

Nov. 21, 1986 [DE] Fed. Rep. of Germany ....... 3639857

[51] Int. Cl.$^4$ .................. C07C 120/00; C07C 120/08
[52] U.S. Cl. .................................... 558/313; 558/311; 558/312; 568/864
[58] Field of Search ................ 558/313, 311, 312, 864

[56] References Cited

U.S. PATENT DOCUMENTS 3,979,432  9/1976  Hagemeyer, Jr. et al. ......... 558/311
4,234,509  11/1980  Billenstein et al. ................ 558/312
4,482,503  11/1984  Hofmann ........................ 558/313 X

FOREIGN PATENT DOCUMENTS 3244752  6/1984  Fed. Rep. of Germany .

*Primary Examiner*—Joseph Paul Brust

[57] ABSTRACT

Glycerides are reacted with ammonia in an amount of at least 200 liters per kilogram of glyceride per hour, at a temperature of 220° to 300° C., and in the presence of special catalysts. Of the product mixture which is formed and removed from the reaction with the excess ammonia, and which is composed essentially of the components water, the desired glycerol and fatty acid nitrile containing fatty acid and fatty acid amide, the latter component is returned to the reaction during the glyceride reaction. After completion of the glyceride reaction, which is indicated when the product mixture contains virtually no more glycerol, all the fatty acid nitrile containing fatty acid and fatty acid amide is further treated, in an after-reaction with a reduced amount of ammonia and at higher temperature, in order to convert the fatty acid and fatty acid amide impurities into fatty acid nitrile.

6 Claims, No Drawings

PROCESS FOR THE PREPARATION OF FATTY ACID NITRILES AND GLYCEROL FROM GLYCERIDES

The invention relates to a process for the simultaneous preparation of fatty acid nitriles and glycerol from glycerides, in which the glyceride is reacted, in a reaction vessel at a temperature of 220° to 300° C., with ammonia in an amount of at least 200 liters per kilogram of glyceride per hour, in the presence of catalysts selected for this reaction, and the product mixture which is formed in the glyceride reaction (or main reaction) is discharged from the reaction vessel until the discharged product mixture, which is essentially composed of water, glycerol and fatty acid nitrile containing fatty acid and fatty acid amide, contains virtually no more glycerol (end of the glyceride reaction or of the main reaction), and in which thereafter (that is to say after completion of the glyceride reaction or glycerol discharge) the fatty acid nitrile containing fatty acid and fatty acid amide is returned to the reaction vessel and is further reacted, in the presence of the abovementioned catalyst at a temperature of 240° to 320° C., with ammonia in an amount of 5 to 150 liters per kilogram of the total fatty acid nitrile containing fatty acid and fatty acid amide which is present in the reaction vessel, per hour (after-reaction) until all the fatty acid and all the fatty acid amide have been converted into fatty acid nitrile (end of the after-reaction).

A process of this type is disclosed in U.S. Pat. No. 4,234,509 (which is equivalent to European Patent 0,000,916). In this, the discharged fatty acid nitrile containing fatty acid and fatty acid amide is, after completion of the glyceride/ammonia reaction (after the end of the main reaction), introduced into the reaction vessel in which, under the stated conditions, in a reaction called the after-reaction the conversion of all the fatty acid present and of all the fatty acid amide present into fatty acid nitrile takes place (cf. U.S. Pat. No. 4,234,509, in particular column 7, from line 54, and claim 8). Thus, in this process, in a 1st stage the glyceride which is used is reacted with ammonia until virtually all the expected glycerol has been discharged, and thereafter this reaction is stopped. Only then is the fatty acid nitrile which has collected up to this time as the 2nd phase (in addition to the glycerol phase) in a receiver, which is optionally heated to 60° to 120° C., and which has a greater or lesser content of fatty acid and fatty acid amide (both of which are undesired and thus are to be converted into fatty acid nitrile) introduced into the reaction vessel (to join the product residue which is still present therein and is likewise essentially composed of fatty acid nitrile containing fatty acid and fatty acid amide), and the contents of the reaction vessel, that is all the (contaminated) crude fatty acid nitrile, reacted, in the presence of the abovementioned catalyst at a temperature of 240° to 320° C., with ammonia in an amount of 5 to 150 per kg of crude fatty acid nitrile per hour, until the fatty acid and fatty acid amide have been converted into fatty acid nitrile (in this reaction virtually only water of reaction and excess ammonia are now discharged from the reaction vessel).

It has emerged that the process for the preparation of fatty acid nitrile and glycerol from glycerides which is described in U.S. Pat. No. 4,234,509 has some disadvantages. Thus, owing to the time between the main reaction and the start of the after-reaction, it has to be accepted that the batch time will be relatively long. In particular, the quality of the glycerol leaves something to be desired. It not only contains a considerable amount of water, it is often also contaminated with fatty acid, fatty acid amide and fatty acid nitrile. All the examples in U.S. Pat. No. 4,234,509 (including Example 16 in which the known process described in the introduction is explained in detail) show that an extensive water wash is necessary to work up the glycerol and crude fatty acid nitrile which have collected in the receiver. It is necessary, in particular, to wash the crude fatty acid nitrile with water after the end of the main reaction and before introduction into the reaction vessel, because it contains not only fatty acid and fatty acid amide but also glycerol, which must be removed before the said introduction, because otherwise it remains in the fatty acid nitrile, and because it would be at least partially decomposed at the relatively high temperatures of the after-reaction (formation of color and odor).

U.S. Pat. No. 4,234,509 describes not only the procedure for the preparation of fatty acid nitrile and glycerol from glycerides which has been described above but also, as another variant, one in which the discharged product mixture is subjected to a fractionation before the phase-separation, and the fatty acid and fatty acid amide which are removed from the fatty acid nitrile and glycerol during this are continuously returned to the reaction (cf. US Patent, Col. 7, from line 23, and claim 7). It has emerged that this 2nd procedure has even more disadvantages than the 1st, especially since the resulting fatty acid nitrile is still not entirely satisfactory in terms of color and odor. Finally, certain diorganotin sulfonates are recommended in German Offenlegungsschrift No. 3,244,752 as catalysts for the reaction under discussion. Although better yields of glycerol and fatty acid nitrile are obtained with these, once again the abovementioned disadvantages relating to the purity of the two products, in particular relating to the purity of the glycerol, apply.

Accordingly, the object of the invention is to improve the process mentioned in the introduction in such a way that the disadvantages which have been detailed are substantially eliminated or no longer present. This is achieved according to the invention, surprisingly, by the discharged fatty acid nitrile containing fatty acid and fatty acid amide being returned to the reaction during the glyceride reaction, in place of return after the glyceride reaction, with the abovementioned temperature of 240° to 320° C., and the abovementioned ammonia amount of 5 to 150 (which are the conditions of the after-reaction), being set up as soon as the glyceride reaction is virtually complete.

Thus, in the process according to the invention the fatty acid nitrile containing fatty acid and fatty acid amide (also called crude fatty acid nitrile) is returned to the reaction during the glyceride reaction. In contrast to this, in the state of the art the crude fatty acid nitrile is not further treated until after the end of the glyceride reaction, or it is not the crude fatty acid nitrile, but only the fatty acid amide which has been removed, and the fatty acid which has been removed, therefrom by fractionation, which is returned to the reaction.

It was surprising that using the procedure according to the invention such a beneficial effect is obtained that the abovementioned disadvantages of the known processes are virtually eliminated. An essential reason for the unexpectedly great effect is probably that the return of the crude fatty acid nitrile according to the invention, in particular the fatty acid nitriles contained therein, gives rise to what may be called an entrainment effect, through which a distinct, that is to say continuous and rapid, discharge of the glycerol is achieved.

The return of crude fatty acid nitrile according to the invention is preferably carried out continuously or stepwise. The continuous return is preferably effected in such a way that the amount of crude fatty acid nitrile discharged per unit time during the glyceride reaction is returned in essentially the same unit time and in essentially the same amount. The stepwise return is preferably effected in such a way that a defined amount of crude fatty acid nitrile is returned in each fixed time interval. Of the two variants, continuous return is preferred. The return of crude fatty acid nitrile is, as a rule, not started immediately after the discharge begins, because, as is clear, it has first to be removed from the glycerol and water which have been discharged at the same time as it. In a preferred embodiment of the process according to the invention, in the same way as in the known process the product mixture formed in the glyceride reaction is discharged via a condensing device into a heated receiver. The preferred process according to the invention, in which the product mixture is discharged from the reaction vessel via a line which is connected to a condensing device, and in which the product components glycerol and fatty acid nitrile containing fatty acid and fatty acid amide which have condensed in the condensing device are deposited in a heated receiver as a lower glycerol phase and an upper fatty acid nitrile phase containing fatty acid and fatty acid amide (crude fatty acid nitrile), comprises the connecting line from the reaction vessel to the condensing device being heated during the glyceride reaction essentially to the temperature which corresponds to the reaction temperature, and comprises the fatty acid nitrile which contains fatty acid and fatty acid amide and which is deposited in the receiver being returned to the reaction during the glyceride reaction. In this embodiment of the process according to the invention too, the return of crude fatty acid nitrile is preferably carried out continuously or stepwise, the continuous return being preferred. This is achieved in a straightforward manner by crude fatty acid nitrile continuously flowing back out of the receiver into the reaction vessel via a line which connects the top of the receiver with the top of the reaction vessel. The flowing back will not start until the receiver has been filled with glycerol as lower phase and crude fatty acid nitrile as upper phase. The resulting more or less short time interval between the start of the discharge and the start of the return of crude fatty acid nitrile is negligible compared with the overall reaction time of the glyceride reaction. The return of crude fatty acid nitrile into the reaction is expediently started no later than when up to 20% by weight, preferably up to 15% by weight, of the total expected glycerol/crude fatty acid nitrile mixture has already been discharged. Moreover, not all the discharged crude fatty acid nitrile will be returned, because it is unavoidable that a residue, which depends on the size of the receiver, of crude fatty acid nitrile remains. This residue is very small compared with the total crude fatty acid nitrile. Thus, in the described manner of returning crude fatty acid nitrile to the glyceride reaction, the amount of crude fatty acid nitrile discharged per unit time during the reaction is essentially returned in the same unit time and essentially in the same amount. Besides the return of crude fatty acid nitrile into the glyceride reaction, according to the invention the line through which the product mixture reaches the condensing device is heated, specifically to that temperature which is essentially equal to the reaction temperature during the glyceride reation. Essentially the whole of the piece of line between the top of reaction vessel and of the condensing device is maintained at the temperature under discussion. The heating is expediently effected with the aid of an electric heater, for example with an electric heating jacket, which is placed around the line, or with the aid of a heating fluid which circulates in the encasing jacket with which the line is provided. The condensing device, which takes the form of, for example, a condenser and into whose lower part the connecting line from the reaction vessel opens, is controlled in such a way that the said components glycerol and crude fatty acid nitrile condense essentially completely, whereas the water of reaction and the excess ammonia emerge in the form of gases.

It is preferred according to the invention for the receiver, and thus its contents, that is the glycerol phase and the crude nitrile phase, to be heated to a temperature of 60° to 200° C., preferably 140° to 175° C., and to be maintained at this temperature until the glyceride reaction (the main reaction) is virtually complete. It is also possible during the after-reaction for the receiver to be maintained at the temperature which is to be set up according to the invention. The receiver is expediently heated with the aid of an electric heater, for example with an electric heating jacket which is placed around the receiver, or with the aid of a heating fluid which circulates in the encasing jacket with which the receiver is provided. The heating of the receiver according to the invention results in the two phases being virtually free of water and ammonia and, moreover, being completely separated from one another, which means that the glycerol phase contains virtually no crude nitrile, and the crude nitrile phase contains virtually no glycerol. The result of this is that the glycerol which is removed from the receiver as lower phase is already highquality glycerol. The effect achieved by the heating of the receiver according to the invention can be further increased if the glycerol phase is gently agitated. Accordingly, in the preferred embodiment of the process according to the invention the preferred procedure is specifically such that the connecting line between reaction vessel and condensing device, and the receiver, are heated to the temperatures which are to be set up according to the invention, the product mixture which reaches the receiver from the condensing device at the start of the glyceride reaction and which is virtually free of water and ammonia is allowed to settle into a lower glycerol phase and into an upper crude fatty acid nitrile phase, and after the receiver has filled the amount of crude fatty acid nitrile which has continuously reached the receiver with the crude fatty acid nitrile/glycerol mixture is simply allowed to flow back via the line from the receiver to the reaction vessel. After the end of the main reaction, the contents of the reaction vessel (that is the total crude fatty acid nitrile) are treated under the conditions of the after-reaction. In this procedure the desired glycerol is drawn off from the receiver as lower phase, and the desired fatty acid nitrile is drawn off from the reaction vessel after completion of the after-reaction. The discharge of the glycerol from the receiver can take place continuously, specifically in essentially the amount which reaches the receiver and settles out there as lower phase.

Using the process according to the invention, a particularly pure glycerol and a particularly pure fatty acid nitrile are simultaneously and directly obtained in high yield. Hence there is no need for the two products to be subjected to laborious and time-consuming purification operations, such as degassing and water washing. The resulting glycerol is virtually a high-quality glycerol. Although the fatty acid nitrile which is obtained at the same time still contains the catalyst which is used, it is virtually free of particularly undesired fatty acid and fatty acid amide impurities. It is easy to remove the catalyst, for example by distillation. Furthermore, in the process according to the invention the glyceride reaction is accomplished in a shorter time than in the known process variants. This is evidently a result of the new return technique. The overall reaction time is also decreased further by there being no loss of time between the main reaction and the after-reaction. The process according to the invention therefore has a shorter batch time than the known process variants. Compared with the latter, it is more straightforward and results, in a particularly economical manner, in pure products in high yield.

Concerning the measures in the process according to the invention which are known per se, reference may be made to the publications mentioned in the introduction, U.S. Pat. No. 4,234,509 and European Patent 0,000,916, in which these measures, as well as the suitable glycerides (the starting materials), are described in detail. In the process according to the invention too, the starting materials are mono-, di- or triglycerides of the following formulae

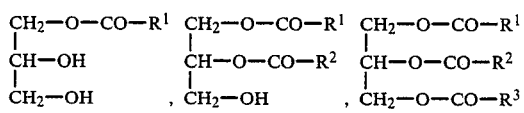

(including structural isomers) or mixtures thereof, which result in the nitriles of the formulae $R^1$—CN, $R^2$—CN and $R^3$—CN.

In these formulae, in the case of di- and triglycerides $R^1$ and $R^2$ or $R^1$, $R^2$ and $R^3$ can be identical or can be different. The radicals $R^1$, $R^2$ and $R^3$ are selected from the following groups:

(a) alkyl radicals, which can be branched but are preferably straight-chain, having 3 to 23, preferably 7 to 23, carbon atoms;

(b) olefinically unsaturated aliphatic hydrocarbon radicals, which can be branched but are preferably straight-chain, having 3 to 23, preferably 11 to 21, and in particular 15 to 21, carbon atoms, and having 1 to 6, preferably 1 to 3, double bonds, which can be conjugated or isolated; and (c) monohydroxy-substituted radicals of type (a) and (b), preferably the unsaturated hydrocarbon radicals which contain 1 to 3 double bonds, in particular the radical of ricinoleic acid.

The acyl radicals $R^1$—CO—, $R^2$—CO— and $R^3$—CO— of the glycerides which are suitable as starting materials for the process of the present invention are derived from the following groups of aliphatic carboxylic acids (fatty acids):

(a) alkanoic acids and their alkyl-branched, preferably methyl-branched, derivatives, having 4 to 24 carbon atoms, such as, for example, butyric acid, valeric acid, caproic acid, heptanoic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, 2-methylbutanoic acid, isobutyric acid, isovaleric acid, pivalic acid, isocaproic acid, 2-ethylcaproic acid, the positional isomers of methylcapric acid, methyllauric acid and methylstearic acid, 12-hexylstearic acid, isostearic acid or 3,3-dimethylstearic acid;

(b) alkenoic acids, alkadienoic acids, alkatrienoic acids, alkatetraenoic acids, alkapentaenoic acids and alkahexaenoic acids and their alkyl-branched, preferably methylbranched, derivatives, having 4 to 24 carbon atoms, such as, for example, crotonic acid, isocrotonic acid, caproleic acid, linderic acid, lauroleic acid, myristoleic acid, palmitoleic acid, petroselic acid, oleic acid, elaidic acid, erucic acid, brassidic acid, 2,4-decadienoic acid, linoleic acid, 11,14-eicosadienoic acid, hiragonic acid, eleostearic acid, linolenic acid, pseudoeleostearic acid, arachidonic acid, 4,8,12,15,18,21-tetracosahexaenoic acid or trans-2-methyl-2-butenoic acid;

(c) monohydroxyalkanoic acids having 4 to 24 carbon atoms, preferably 12 to 24 carbon atoms, preferably unbranched, such as, for example, hydroxybutyric acid, hydroxyvaleric acid, hydroxycaproic acid, 2-hydroxydodecanoic acid, 2-hydroxytetradecanoic acid, 15-hydroxypentadecanoic acid, 16-hydroxyhexadecanoic acid or 18-hydroxyoctadecanoic acid; and (d) monohydroxyalkenoic acids having 4 to 24, preferably having 12 to 22, and in particular having 16 to 22, carbon atoms (preferably unbranched) and having 1 to 6, preferably having 1 to 3, and in particular having one, ethylenic double bond, such as, for example, ricinoleic acid or ricinelaidic acid.

Particularly preferred starting materials for the process according to the invention are the natural (vegetable) or animal fats and oils which are mixtures of, predominantly, triglycerides with small contributions from diglycerides and/or monoglycerides, these glycerides in turn usually also being mixtures and containing various types of fatty acid residues in the abovementioned range, in particular those having 8 or more carbon atoms. Examples which may be mentioned are vegetable fats and oils such as olive oil, coconut oil, palm kernel butter, babassu oil, palm oil, peanut oil, rape oil, castor oil, sesame oil, cotton oil, sunflower oil, soybean oil, hemp oil, poppy seed oil, avocado oil, cotton seed oil, wheatgerm oil, corn oil, pumpkin seed oil, grape seed oil, cocoa butter or vegetable tallows, furthermore animal fats and oils, such as beef tallow, pork fat, bone fat, mutton tallow, japan wax, whale oil and other fish oils, as well as fish liver oil. It is equally possible to use homogeneous tri-, di- and monoglycerides or mixtures thereof, whether these have been isolated from natural fats or obtained by means of synthesis. Examples which may be mentioned in this connection are: tributyrin, tricapronin, tricaprylin, tricaprinin, trilaurin, trimyristin, tripalmitin, tristearin, triolein, trielaidin, trilinolein, trilinolenin, monopalmitin, monostearin, monoolein, monocaprinin, monolaurin, monomyristin or mixed glycerides, for example palmitodistearin, distearoolein, dipalmitoolein and myristopalmitostearin.

The catalysts to be used according to the invention are, as they are in the known process, selected special catalysts as described in the publications mentioned in the introduction, U.S. Pat. No. 4,234,509 and German Offenlegungsschrift No. 3,244,752 A1. These catalysts are selected from the group comprising (a) metal salts of carboxylic acids or sulfonic acids, the metal cation in the metal salt being antimony, lead, cadmium, chromium, iron, cobalt, manganese, nickel, titanium, zinc, tin or zircon, preferably lead, cadmium, iron, cobalt or zinc, and (b) diorganotin(IV) bissulfonates of the formula

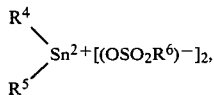

in which $R^4$, $R^5$ and $R^6$, which are identical or different, denote an alkyl radical, aryl radical, alkyl-substituted aryl radical, aralkyl radical or a cycloalkyl radical.

The carboxylic acid or sulfonic acid anion of the said metal salts originates from one of the following groups: (1) saturated aliphatic mono- or polycarboxylic acids, preferably the monocarboxylic acids, having 4 to 24, preferably 8 to 24, carbon atoms, which can be branched but are preferably straight-chain; (2) olefinically unsaturated mono- or polycarboxylic acids, preferably the monocarboxylic acids, having 1 to 6, preferably 1 to 3, isolated or conjugated double bonds and having 4 to 24, preferably 8 to 24, carbon atoms, which can be branched but are preferably straight-chain; (3) mono-, di- or trialkylated, preferably mono- or dialkylated, benzene- or naphthalene- mono- or -polycarboxylic acids, preferably the monocarboxylic acids, having alkyl radicals having 1 to 24, preferably 1 to 12, carbon atoms, it being possible for these alkyl radicals to be branched, but preferably being straightchain; (4) alkanemono- or alkanedisulfonic acids, preferably the monosulfonic acids, having 4 to 24, preferably 8 to 24 carbon atoms, which can be branched but are preferably straight-chain; (5) fluoro-substituted alkanemonosulfonic acids, preferably perfluoro-substituted, having 4 to 24, preferably 8 to 24, carbon atoms, which can be branched but are preferably straight-chain; (6) monohydroxy-substituted alkanemonosulfonic acids having 4 to 24, preferably 8 to 24, carbon atoms, which can be branched but are preferably straight-chain; (7) mono-, di- or trialkylated, preferably mono- or dialkylated, benzene-or naphthalenemono- or polysulfonic acids, preferably the monosulfonic acids, having alkyl radicals having 1 to 24, preferably 1 to 12, carbon atoms, it being possible for these alkyl radicals to be branched, but preferably being straight-chain; and (8) (monocarboxy)alkyl- or (dicarboxy)- alkyl-substituted benzene- or naphthalenemono- or -polysulfonic acids, preferably the (monocarboxy)alkyl-substituted monosulfonic acids, having alkyl radicals having 1 to 24, preferably 1 to 12 carbon atoms.

Concerning the diorganotin sulfonates of the abovementioned formula, those preferred have $R^4$, $R^5$ and $R^6$ with the meanings indicated hereinafter: $R^4$ and $R^5$, which are preferably identical, denote straight-chain or branched alkyl radicals having 1 to 22, preferably 4 to 18, carbon atoms; aryl radicals, preferably phenyl or naphthyl radicals each of which can be substituted with 1 to 3 straight-chain or branched alkyl radicals each having 1 to 22, preferably 1 to 12, carbon atoms, the monosubstituted aryl radicals being preferred; aralkyl radicals, preferably the benzyl radical; or cycloalkyl radicals, preferably the cyclohexyl radical. $R^6$, which can be different from $R^4$ and $R^5$ or identical to one or both of these radicals, denotes an alkyl radical having 4 to 24, preferably 8 to 24, carbon atoms, which can be straight-chain or branched; an aryl radical, preferably the phenyl or the naphthyl radical, which can be substituted with 1 to 3, preferably with one straight-chain or branched alkyl radical having 1 to 22, preferably 1 to 12, carbon atoms; or an aralkyl radical, preferably the benzyl radical.

In the case of metal salts of carboxylic acids or sulfonic acids as catalysts, those particularly preferred have lead, cadmium, iron, cobalt or zinc as the metal cation, and the anion is selected from the representatives (4), (6) and (7) listed above, preference being given to the alkanemonosulfonic acids and the alkylarylsulfonic acids, thus, for example, n-octanesulfonic acid, n-dodecylsulfonic acid, n-octadecylsulfonic acid, $C_{15}-C_{18}$-alkanesulfonic acid, tallow fatty acid, methylbenzene(toluene)sulfonic acid, n-hexylbenzenesulfonic acid, n-dodecylbenzenesulfonic acid, n-butylnaphthalenesulfonic acid and n-dodecylnaphthalenesulfonic acid. In the case of diorganotin sulfonates as catalysts, those particularly preferred emerge from the above formula when $R^4$ and $R^5$, which are preferably identical, denote an alkyl radical having 1 to 22, preferably 4 to 18, carbon atoms, a phenyl radical or a naphthyl radical, and $R^6$ is an alkyl radical having 4 to 24, preferably 8 to 24, carbon atoms, or an aryl radical which is composed of an unsubstituted phenyl radical or of a phenyl radical which is substituted with an alkyl radical having 1 to 22, preferably 1 to 12, carbon atoms. The said catalysts are used in an amount of from 0.5 to 10% by weight, preferably 1 to 5% by weight, based on the glyceride. As a rule, they are added as such to the glyceride. It is also possible to add the appropriate metal oxide and the appropriate carboxylic acid or sulfonic acid singly, there then being formation of this catalyst in situ during the reaction. It is equally possible in the case of the organotin catalyst to add the starting organotin compounds (oxides, hydroxides, fatty acid salts) and the free sulfonic acids, there likewise then being formation of the diorganotin(IV) bissulfonate compounds in situ.

Concerning the measures known per se in the process according to the invention, once again the amount of ammonia which is passed through the glyceride which is heated in the reaction vessel is at least 200 liters per kilogram of glyceride per hour, preferably at least 400 liters per kilogram of glyceride per hour. There is no critical upper limit in respect of the ammonia flow to be passed through, the upper limit in terms of quantity will be determined only by economic considerations and, on these grounds, will be about 1,000 liters, preferably about 800 liters, of ammonia per kilogram of glyceride per hour. The amount of ammonia is thus generally 200 to 1,000 liters, preferably 400 to 800 liters, per kilogram of glyceride per hour, and it is possible with advantage to add thereto up to 30% by volume, preferably up to 15% by volume, based on the amount of ammonia passed through, of inert gas, for example nitrogen. Passing the said ammonia flow through the glyceride which has been heated to 220° to 300° C. (and thus is in the form of a liquid phase) ensures good contact between glyceride and ammonia as well as rapid discharge from the reaction vessel of the glycerol which is formed and, equally of the crude fatty acid nitrile and water of reaction which are formed. As already mentioned, the glyceride is heated to a temperature of 220° to 300° C., preferably 230° to 270° C. This reaction temperature is maintained throughout the glyceride reaction, that is to say until the initially introduced glyceride releases virtually no more glycerol (end of the main reaction). It is preferred for the temperature to rise from the start to the end of the reaction, either continuously or stepwise, especially in the form of a temperature programme. In a preferred embodiment, the reaction (main reaction) is initially carried out in the temperature range of about 220° to 240° C. until about 30 to 70% by weight of the theoretically expected amount of glycerol has been discharged from the reaction vessel. The temperature is then raised, stepwise or continuously, over the course of about ½ to 5 hours to about 250° to 270° C., whereupon the reaction is driven to completion at the elevated temperature. The end of the reaction can be recognized from the fact that no more, or virtually no more, glycerol enters the receiver. After completion of the main reaction, the conditions of the after-reaction are set up in just the same way as in the known process. All the crude fatty acid nitrile present in the reaction vessel (that is the fatty acid nitrile containing fatty acid and fatty acid amide which has been returned according to the invention during the main reaction and that remaining in the reaction vessel) is heated to a temperature of 240° to 320° C., preferably 260° to 300° C., and the ammonia flow is adjusted to 5 to 150 liters, preferably 15 to 100 liters, per kilogram of crude fatty acid nitrile per hour, and is passed through the contents of the reaction vessel (which is in the form of a liquid phase). Using these conditions of reaction temperature and amount of ammonia, in the presence of the catalysts used for the main reaction the fatty acids and fatty acid amides contained in the crude fatty acid nitrile are converted into fatty acid nitriles, the resulting water of reaction being discharged from the reaction vessel. Where fatty acid nitriles, fatty acids and/or fatty acid amides are also to be discharged with the ammonia flow, these components are returned to the reaction vessel. If sufficient catalysts have already been used for the main reaction (an amount of catalyst which is at the upper limit of the abovementioned ranges of amounts) it is unnecessary again to add catalyst. Otherwise, an appropriate amount of catalyst should be added. The amount of catalyst in the after-reaction is in the range 0.5 to 10% by weight, preferably 1 to 5% by weight, based on the weight of the crude fatty acid nitrile. With these reaction conditions there is complete conversion of fatty acid amides and fatty acids into fatty acid nitriles, it being possible to follow the conversion by the formation of water of reaction, which is discharged with the excess ammonia. In just the same way as with the main reaction, it is possible to return the excess ammonia flow, from which reaction components and water of reaction have expediently been completely removed, where appropriate after addition of fresh ammonia, to the reaction. After completion of the after-reaction it is possible to draw off the desired fatty acid nitrile which is present in the reaction vessel. As already mentioned above, the catalyst which is still present in this fatty acid nitrile which is pure per se can be removed by distillation, for example.

The invention is now illustrated in more detail by examples.

EXAMPLE 1

In this example according to the invention, crude fatty acid nitrile is continuously returned to the reaction during the glyceride reaction. 500 g of carcass fat (saponification number 185, acid number 13.9) and 10 g of zinc dodecylbenzenesulfonate as catalyst (which is 2% by weight of catalyst, based on the fat or glyceride) were initially introduced into a reaction vessel. The reaction vessel had a capacity of 700 ml and was equipped with a heating device for heating the contents to the reaction temperature, a stirrer for stirring the contents, and an internal thermometer for determining the prevailing temperature, and a gas inlet line for the ammonia flow. The reaction vessel was connected to a cooling column (a condenser) which was located above and to one side of the reaction vessel. The line from the top of the reaction vessel into the lower part of the cooling column was equipped with an electric heater. The foot of the cooling column was connected to a cylindrical vessel of capacity 100 ml for receiving and depositing the condensed phase components. A line led from the vessel, that is the receiver, back to the reaction vessel. This line went from the top of the receiver to the top of the reaction vessel and was inclined towards the reaction vessel so that flow from the receiver to the reaction vessel could take place.

The reaction vessel was flushed with nitrogen during the heating up. At 150° C., the nitrogen was replaced by gaseous ammonia, which was circulated in an amount of 600 liters of ammonia per kilogram of carcass fat (tallow) per hour. The reaction vessel, and thus the contents of the reaction vessel, was heated to 230° C. (start of the glyceride reaction or main reaction) and maintained at this temperature for 3 hours. During the reaction, fresh gaseous ammonia was continuously added in order to maintain the stated 600 liters of ammonia. After the reaction time of 3 hours, the temperature was increased from 230° to 260° C. within about 1.5 hours, and the temperature of 260° C. was maintained for 30 minutes. After this time, that is a reaction time of 5 hours, there was virtually no more glycerol in the discharged product mixture, which indicated the end of the reaction between the tallow used and the ammonia (end of the glyceride reaction or of the main reaction). During the glyceride reaction, which started at the temperature of 230° C., the product mixture formed, essentially composed of glycerol, crude fatty acid nitrile and water, was discharged with the excess ammonia flow from the reaction vessel into the cooling column via the connecting line, which was heated initially to 230° C. and then up to 260° C., from the reaction vessel to the cooling column (the specific heating according to the invention of the connecting line under discussion results in condensation of glycerol in this line, and thus flow of glycerol back into the reaction vessel, being ruled out). The two components, glycerol and crude fatty acid nitrile (the latter contained about 2% by weight of fatty acid and 3% by weight of fatty acid amide), condensed virtually completely in the cooling column and collected in the receiver, with a lower glycerol phase and an upper crude fatty acid nitrile phase separating out. The ammonia and essentially all the water left the cooling column in the form of gases (the ammonia was, after removal of the water, returned to the reaction vessel). The receiver, and thus its contents, was maintained at a temperature of 150° C., by which means any residual water still present and dissolved ammonia were removed. The glycerol phase was continuously agitated using a magnetic stirrer, in order to speed up and complete the said degassing of ammonia. After a reaction time of about 30 min, the receiver, with a capacity of 100 ml, contained about 90 ml, which filled it to the point of attachment of the connecting line to the reaction vessel (which means to the overflow). In this time, about 15% by volume of glycerol plus crude fatty acid nitrile, based on the expected total amount of glycerol and crude fatty acid nitrile, had been discharged (the 90 ml comprised about 8 ml of glycerol and 82 ml of crude fatty acid nitrile). After the receiver had filled, the crude fatty acid nitrile necessarily began to flow back via the connecting line into the reaction vessel. Thus, from now on, there was continuous flow back into the reaction of an amount of crude fatty acid nitrile essentially identical to that formed during the reaction of the fat with ammonia and discharged together with the glycerol and the water of reaction with the ammonia flow (the connecting line from the receiver to the reaction vessel was heated to the temperature corresponding to the reaction temperature in order to prevent cooling of the flow back through the connecting line and thus any cooling in the reaction vessel). After the end of the glyceride reaction, that is to say after the said reaction time of 5 hours, the desired glycerol was drawn off from the receiver. The amount of crude fatty acid nitrile present in the receiver was placed in the reaction vessel (this amount of crude fatty acid nitrile is very low compared with the total amount of crude fatty acid nitrile). The temperature of the reaction vessel, in which the entire amount of crude fatty acid nitrile was present, was raised to 300° C., and the ammonia flow was reduced to 100 liters of ammonia per kilogram of crude fatty acid nitrile per hour. These conditions (that is the conditions of the after-reaction) were maintained for 1.5 hours. The water of reaction formed in the after-reaction was discharged with the excess ammonia flow via the connecting line, which was now no longer heated, and the cooling column. Despite the low ammonia flow, any fatty acid nitrile which was carried with it did condense in the, no longer heated, connecting line and flowed back into the reaction vessel (at the start of the after-reaction, the receiver was removed from the reaction vessel and from the cooling column because it was no longer needed). After the said reaction time of 1.5 hours, the components which were to be transformed, the fatty acid and fatty acid amide, had been transformed into fatty acid nitrile. The fatty acid nitrile which was pure per se, now containing only catalyst, was drawn off from the reaction vessel, and the catalyst was removed in a distillation.

The following yields and purities were achieved: Glycerol yield: 38 ml (45 g) which is 90% of theory; the glycerol contained virtually no water, fatty acid, fatty acid amide or fatty acid nitrile and thus was already a pure glycerol without any further purification operation. Fatty acid nitrile yield: 533 ml (426 g) which is 95% of theory; the fatty acid nitrile contained no glycerol or water and had only residual contents of 0.25% by weight of fatty acid amide and 0.2% by weight of fatty acid.

EXAMPLE 2

In this example according to the invention, crude fatty acid nitrile was returned stepwise to the reaction during the glyceride reaction.

The example was carried out with the same reaction components and with the same reaction conditions as was Example 1, with the difference that the crude fatty acid nitrile formed and removed during the glyceride reaction was returned to the reaction in portions, not continuously. For this purpose, the apparatus used in Example 1 was modified in such a way that a receiver of capacity 200 ml was taken, and the connecting line from the receiver to the reaction vessel was attached not at the top of the receiver but to its lower part and, moreover, had a shut-off device.

After the receiver had filled to the overflow (15 minutes had elapsed from the start of the glyceride reaction up to this time, and about 5 ml of glycerol and about 40 ml of crude fatty acid nitrile, which is about 8% by volume of the total expected amount of glycerol plus crude fatty acid nitrile, had been discharged and deposited in the receiver), and after flow back of crude fatty acid nitrile had necessarily been maintained for about 30 minutes, the flow back was stopped by means of the said shut-off device so that the crude fatty acid nitrile collected in the receiver. About 40 ml of crude fatty acid nitrile had collected after 15 minutes. This amount of crude fatty acid nitrile was now allowed, by opening the shut-off device, to flow back into the reaction vessel (metering in) within about 5 minutes, whereupon the shut-off device was closed again in order to collect the same amount of crude fatty acid nitrile. The procedure of collection and stepwise return (in portions) of crude fatty acid nitrile which has been described was repeated 9 more times until the end of the glyceride reaction, which was reached after 5 hours. After the end of the glyceride reaction, the procedure was continued as in Example 1.

The following yields and purities were achieved: Glycerol yield: 38 ml (45 g) which is 90% of theory; the glycerol contained virtually no water, fatty acid, fatty acid amide or fatty acid nitrile and thus was already a pure glycerol without any further purification operation. Fatty acid nitrile yield: 533 ml (426 g) which is 95% of theory; the fatty acid nitrile contained no glycerol or water and had only residual contents of 0.25% by weight of fatty acid amide and 0.2% by weight of fatty acid.

The carcass fat used in Examples 1 and 2 was a mixture essentially composed of beef tallow, mutton tallow, pork fat and bone fat.

EXAMPLES 3 to 7

These examples were carried out in analogy to Example 1, but with different glycerides, catalysts, amounts of ammonia ($NH_3$), reaction temperatures and/or reaction times. These variations and the results of the examples are detailed hereinafter (all percentage data are percentages by weight; the first of the two numbers quoted in parentheses after the glyceride which was used is the saponification number, and the second is the acid number; the percentage given after the catalyst compound is the amount of catalyst used).

EXAMPLE 3

Industrial beef tallow (186; 12.6); lead n-dodecylsulfonate, 3%; 400 of $NH_3$ during the glyceride reaction and 100 of $NH_3$ during the after-reaction; reaction temperature for the glyceride reaction 250° C. for 3 hours, and for the after-reaction 280° C. for 1.5 hours. Result: Glycerol yield 86%, fatty acid nitrile yield 93% with 0.13% of fatty acid amide and 0.12% of fatty acid.

EXAMPLE 4

Edible fat (190; 2.4); cadmium n-octadecylsulfonate, 2%; 800 l of $NH_3$ during the glyceride reaction and 100 l of $NH_3$ during the after-reaction; reaction temperature for the glyceride reaction 230° C. for 3 hours, then increased to 260° C. within 1.5 hours (5° C. per 15 minutes), reaction temperature for the after-reaction 300°

C. for 1.5 hours. Result: Glycerol yield 91%, fatty acid nitrile yield 95% with less than 0.1% of fatty acid amide and less than 0.1% of fatty acid.

EXAMPLE 5

Pork fat (124; 11.7); cobalt n-octanesulfonate, 4%; 400 l of $NH_3$ during the glyceride reaction and 15 l of $NH_3$ during the after-reaction; reaction temperature for the glyceride reaction 230° C. for 3 hours, then increased to 250° C. within 1 hour (5° C. per 15 minutes), reaction temperature for the after-reaction 275° C. for 2 hours. Result: Glycerol yield 87%, fatty acid nitrile yield 92% with 0.22% of fatty acid amide and 0.20% of fatty acid.

EXAMPLE 6

Sunflower oil (189; 0.8); iron(II) n-butylnaphthalenesulfonate, 5%; 400 l of $NH_3$ during the glyceride reaction and 50 l of $NH_3$ during the after-reaction; reaction temperature for the glyceride reaction 240° C. for 4 hours and for the after-reaction 300° C. for 1.5 hours. Result: Glycerol yield 87%, fatty acid nitrile yield 91% with 0.20% of fatty acid amide and 0.15% of fatty acid.

EXAMPLE 7

Soybean oil (203; 0.5); di-n-octyltin(IV) bis(toluenesulfonate), 2%; 800 of l $NH_3$ during the glyceride reaction and 50 l of $NH_3$ during the after-reaction; reaction temperatures as in Example 5.0 Result: Glycerol yield 89%, fatty acid nitrile yield 94% with 0.18% of fatty acid amide and 0.10% of fatty acid.

EXAMPLES 8 to 13

These examples were carried out in analogy to Example 2, but with different glycerides, catalysts, amounts of ammonia ($NH_3$), reaction temperatures and/or reaction times. These variations and the results of the examples are detailed hereinafter (all percentage data are percentages by weight; the first of the two numbers quoted in parentheses after the glyceride which was used is the saponification number, and the second is the acid number; the percentage given after the catalyst compound is the amount of catalyst used).

EXAMPLE 8

Palm oil (202; 0.7); zinc $C_{15}/C_{18}$-alkanesulfonate, 3%; 400 l of $NH_3$ during the glyceride reaction and 15 l of $NH_3$ during the after-reaction; reaction temperatures as in Example 5. Result: Glycerol yield 92%, fatty acid nitrile yield 95% with 0.28% of fatty acid amide and 0.23% of fatty acid.

EXAMPLE 9

Coconut oil (240; 1.8); lead salt of tallow fatty acid, 5%; 600 l of $NH_3$ during the glyceride reaction and 100 l during the after-reaction; reaction temperatures as in Example 6. Result: Glycerol yield 84%, fatty acid nitrile yield 94% with 0.24% of fatty acid amide and 0.15% of fatty acid.

EXAMPLE 10

Castor oil (173; 1.8); cadmium methylbenzene(toluene)sulfonate, 3%; 800 l of $NH_3$ during the glyceride reaction and 50 l of $NH_3$ during the after-reaction; reaction temperatures as in Example 3. Result: Glycerol yield 74% fatty acid nitrile yield 65% with 0.20% of fatty acid amide and 0.18% of fatty acid.

EXAMPLE 11

Rape oil (167; 1.8); cobalt n-dodecylnaphthalenesulfonate, 4%; 600 l of $NH_3$ during the glyceride reaction and 50 l of $NH_3$ during the after-reaction; reaction temperatures as in Example 6. Result: Glycerol yield 89%, fatty acid nitrile yield 91% with 0.16% of fatty acid amide and 0.12% of fatty acid.

EXAMPLE 12

Whale oil (189; 6.3); iron hexylbenzenesulfonate 4%; 400 l of $NH_3$ during the glyceride reaction and 50 l of $NH_3$ during the after-reaction; reaction temperatures as in Example 3. Result: Glycerol yield 83%, fatty acid nitrile yield 86% with 0.27% of fatty acid amide and 0.23% of fatty acid.

EXAMPLE 13

Industrial beef tallow (186; 12.6); di-n-butyltin(IV) bis(n-dodecylbenzenesulfonate), 2%; 800 l of $NH_3$ during the glyceride reaction and 100 l of $NH_3$ during the afterreaction. reaction. Reaction temperature for the glyceride reaction 230° C. for 3 hours, then increased to 260° C. within 1.5 hours (5° C. per 15 minutes) and 0.5 hours at 260° C., reaction temperature for the after-reaction 300° C. for 1.5 hours (the same temperature program was followed in Examples 1 and 2). Result: Glycerol yield 93%, fatty acid nitrile yield 96% with 0.14% of fatty acid amide and 0.10% of fatty acid.

EXAMPLES 14 to 17

These examples were carried out in analogy to Example 1, but with mono- or triglycerides as the glyceride, with diorganotin(IV) bissulfonates as catalysts and with different amounts of ammonia, reaction temperatures and/or reaction times. These variations and the results of the examples are detailed hereinafter (the remarks made at this point for Examples 3 to 7 also apply here).

EXAMPLE 14

Glycerol tricaprylate or tricaprylin (159; 2.8); di-n-octadecyltin(IV) bis(n-octadecylsulfonate), 4%; amounts of $NH_3$ as in Example 4; reaction temperatures as in Example 4. Result: Glycerol yield 89%, fatty acid nitrile yield 94% with 0.18% of fatty acid amide and 0.12% of fatty acid.

EXAMPLE 15

Glycerol tristearate or tristearin (187; 6.7); diphenyltin(IV) bis(n-octylsulfonate), 2%; 600 l of $NH_3$ during the glyceride reaction and 50 l of $NH_3$ during the after-reaction; reaction temperatures as in Example 3. Result: Glycerol yield 92%, fatty acid nitrile yield 95% with 0.17% of fatty acid amide and 0.14% of fatty acid.

EXAMPLE 16

Glycerol monolaurate (178; 3.8); diphenyltin(IV) bis(n-hexadecylsulfonate), 3%; 800 l of $NH_3$ during the glyceride reaction and 15 l of $NH_3$ during the after-reaction; reaction temperatures as in Example 6. Result: Glycerol yield 92%, fatty acid nitrile yield 94% with 0.19% of fatty acid amide and 0.12% of fatty acid.

EXAMPLE 17

Glycerol monooleate (172; 4.6); diphenyltin(IV) pis(-phenylsulfonate), 2%; 400 l of $NH_3$ during the glyceride reaction and 100 l of $NH_3$ during the after-reaction; reaction temperatures as in Example 1. Result: Glycerol yield 90%, fatty acid nitrile yield 90% with 0.14% of fatty acid amide and 0.15% of fatty acid.

EXAMPLE 18

The catalysts stated below were used in Example 18, the procedure otherwise being in every respect as in Example 4. The catalysts are: zinc caprylate, zinc stearate, zinc erucate, lead 2-methylbenzoate, zinc 3-n-dodecylbenzoate, cadmium 2-methylnaphthoate, zinc perfluorohexanesulfonate, cobalt 2-hydroxy-n-dodecanesulfonate and a mixture of 1% by weight of zinc n-dodecylbenzenesulfonate and 1% by weight of cadmium toluenesulfonate.

Result: Glycerol yields from 82 to 96% by weight, fatty acid nitrile yields from 89 to 96% by weight with 0.15 to 0.25% by weight of fatty acid amide and 0.10 to 0.20% by weight of fatty acid.

We claim:

1. A process for the production of glycerol and fatty acid nitrile from the reaction of glyceride with ammonia, said process comprising:

reacting a bath of mono-, di-, or tri-glyceride or mixture thereof having alkyl or olefinically unsaturated aliphatic hydrocarbon or monohydroxyalkyl or monohydroxyalkene radicals of 3 to 23 carbon atoms with a flow of ammonia in an amount of at least 200 liters per kilgram of said glyceride per hour in a reaction zone at a temperature of 220° to 300° C. in the presence of a metal salt of a carboxylic or sulfonic acid or a diorganotin(IV) bissulfonate catalyst wherein said diorganotin catalyst is of the formula $$(R^4)(R^5)Sn^{2+}[(OSO_2R^6)^-]_2$$

in which $R^4$, $R^5$ and $R^6$, are identical or different, and are alkyl, aryl, alkyl-substituted aryl, aralkyl or cycloalkyl, thereby forming an effluent product mixture comprising glycerol, water, and fatty acid nitrile containing fatty acid and fatty acid amide, said fatty acid nitrile, fatty acid, and fatty acid amide all having said radicals of 3 to 23 carbon atoms, conveying the resulting effluent product mixture to a separating zone, wherein said fatty acid nitrile containing fatty acid and fatty acid amide is separated from the product mixture and returned to the reaction zone while the reaction between said glyceride and the ammonia is still proceeding at 220° to 300° C., and continuing to maintain the temperature range of 220° to 300° C. until the batch of said glyceride is essentially used up and the effluent product mixture becomes essentially free of glycerol, subsequently, continuing the return of fatty acid nitrile containing fatty acid and fatty acid amide to the reaction zone while decreasing the flow of ammonia to the amount of 5 to 150 liters per kilogram of the total fatty acid nitrile containing fatty acid and fatty acid amide in the reaction zone, per hour, and adjusting the temperature to 240° to 320° C., until essentially all of the fatty acid and fatty acid amide have been converted to fatty acid nitrile, while conveying the fatty acid nitrile product to the separating zone, and recovering fatty acid nitrile and glycerol from said separating zone.

2. The process according to claim 1, wherein the fatty nitrile containing fatty acid and a fatty acid amide is returned to the reaction zone continuously at a flow rate approximately equal to the rate of flow of effluent product mixture from the reaction zone.

3. The process according to claim 1 wherein the effluent product mixture conveyed from the reaction zone is conveyed at essentially the temperature of the reaction zone and is condensed and deposited in a receiving zone heated to 140° to 175° C., in order to form a lower glycerol phase and a higher fatty acid nitrile phase, said fatty acid nitrile phase containing fatty acid and fatty acid amide, said fatty acid nitrile phase being returned to the reaction zone during the reaction between said glyceride and ammonia as well as during the subsequent step when the flow of ammonia is decreased and the temperature is adjusted.

4. The process according to claim 1, wherein the reaction between said glyceride and the ammonia is carried out at a temperature of 230° to 270° C., and wherein, after the batch of glyceride is essentially used up, the temperature and ammonia flow rates are adjusted to and maintained at 260° to 300° C., and an amount of 15 to 100 liters per kilogram per hour, respectively.

5. The process according to claim 1 wherein said glyceride is a naturally-occuring vegetable or animal fat or oil consisting essentially of a triglyceride of the formula $$\begin{array}{l}CH_2-O-CO-R^1\\ |\\ CH-O-CO-R^2\\ |\\ CH_2-O-CO-R^3\end{array}$$

wherein $R^1$, $R^2$, and $R^3$ are identical or different and are branched or straight-chain alkyl of 7 to 23 carbon atoms or olefinically unsaturated aliphatic hydrocarbon radicals of 11 to 21 carbon atoms.

6. The process according to claim 1 wherein the catalyst is a metal salt of a carboxylic or sulfonic acid.

* * * * *